US012788899B2

(12) United States Patent
Koops et al.

(10) Patent No.: US 12,788,899 B2
(45) Date of Patent: Nov. 10, 2026

(54) SYSTEM FOR SELECTIVELY SUPPLYING AT LEAST ONE AND PREFERABLY TWO SUBSTANCES TO A PERSON AND USE THEREOF

(71) Applicant: INREDA DIABETIC B.V., Goor (NL)

(72) Inventors: Robin Koops, Goor (NL); Mickael Gilbert Robert Boulay, Goor (NL)

(73) Assignee: INREDA DIABETIC B.V., Goor (NL)

( * ) Notice: Subject to any disclaimer, the term of this patent is extended or adjusted under 35 U.S.C. 154(b) by 501 days.

(21) Appl. No.: 18/285,828

(22) PCT Filed: Apr. 5, 2022

(86) PCT No.: PCT/EP2022/059010
§ 371 (c)(1),
(2) Date: Oct. 5, 2023

(87) PCT Pub. No.: WO2022/214484
PCT Pub. Date: Oct. 13, 2022

(65) Prior Publication Data

US 2024/0252748 A1 Aug. 1, 2024

(30) Foreign Application Priority Data

Apr. 7, 2021 (NL) ...................................... 2027928

(51) Int. Cl.
*A61M 5/36* (2006.01)
*A61M 5/14* (2006.01)
(Continued)

(52) U.S. Cl.
CPC ............ *A61M 5/36* (2013.01); *A61M 5/1407* (2013.01); *A61M 5/1413* (2013.01);
(Continued)

(58) Field of Classification Search
CPC .. A61M 5/1407; A61M 5/1413; A61M 5/142; A61M 5/14268; A61M 5/16827;
(Continued)

(56) References Cited

U.S. PATENT DOCUMENTS 8,310,415 B2 * 11/2012 McLaughlin ........ A61B 5/7445 345/76
9,682,199 B2 * 6/2017 Walsh ................. A61M 5/5086
(Continued)

FOREIGN PATENT DOCUMENTS

| | | | |
|---|---|---|---|
| EP | 3427778 | A1 | 1/2019 |
| WO | 2012126745 | A2 | 9/2012 |
| WO | 2015106107 | A1 | 7/2015 |

OTHER PUBLICATIONS

International Search Report and Written Opinion for the International Application No. PCT/EP2022/059010, mailed Jul. 15, 2022, 9 pages.

*Primary Examiner* — Kyle Robert Thomas
(74) *Attorney, Agent, or Firm* — KDW Firm PLLC

(57) ABSTRACT

A system for selectively supplying a substance to a person, for regulating the concentration of glucose in the blood of a person, includes a device for selectively supplying a substance which includes a port for connecting to a transport element, and a controller for controlling the device, an infusion set including an infusion element comprising a first connector for connecting to a second connector of the transport element, and a transport element including second and third connectors. The following parts of the system can form at least one pair: the infusion elements; the second connectors; second connector with said or a respective third connector; or combinations thereof. The device can detect and/or be inputted with information indicating the pair is formed, and the controller controls the device such that a
(Continued)

Figure 1A:
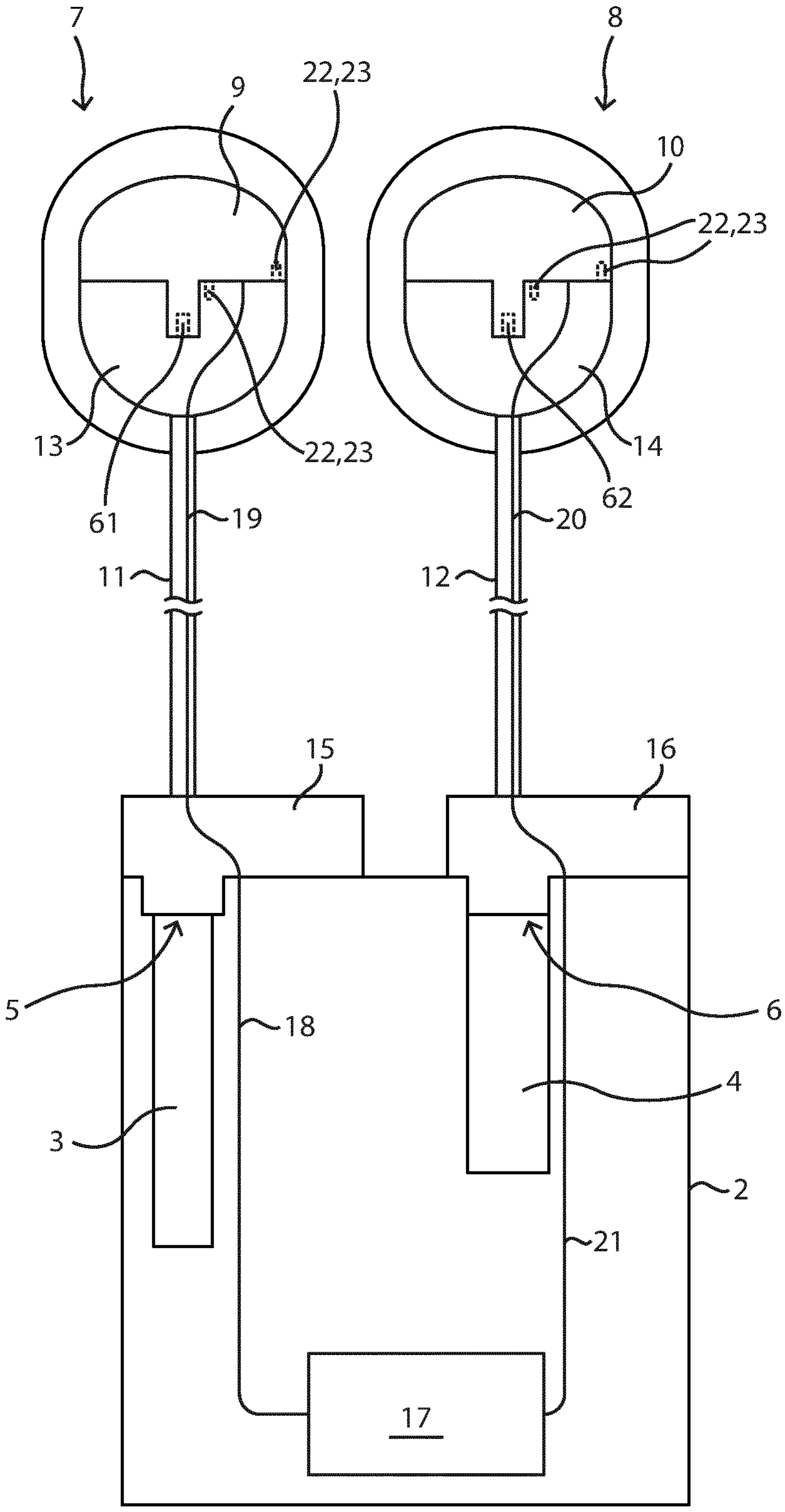

priming function can only be performed if detected and/or inputted that said at least one pair is formed.

16 Claims, 6 Drawing Sheets

(51) Int. Cl.
*A61M 5/142* (2006.01)
*A61M 5/168* (2006.01)
*A61M 5/172* (2006.01)

(52) U.S. Cl.
CPC ........ *A61M 5/142* (2013.01); *A61M 5/16827* (2013.01); *A61M 5/1723* (2013.01); *A61M 2005/1402* (2013.01)

(58) Field of Classification Search
CPC .................. A61M 5/1723; A61M 5/36; A61M 2005/1402; A61M 2202/0486; A61M 2205/14
See application file for complete search history.

(56) References Cited

U.S. PATENT DOCUMENTS

| | | | | |
|---|---|---|---|---|
| 10,549,084 | B2 * | 2/2020 | Sokolov | A61M 39/1011 |
| 11,571,507 | B2 * | 2/2023 | Damiano | A61M 5/162 |
| 2014/0374353 | A1 | 12/2014 | Wright | |
| 2021/0030949 | A1 * | 2/2021 | Damiano | A61M 39/105 |

* cited by examiner

SYSTEM FOR SELECTIVELY SUPPLYING AT LEAST ONE AND PREFERABLY TWO SUBSTANCES TO A PERSON AND USE THEREOF

This application is a national stage filing under 35 U.S.C. 371 of pending International Application No. PCT/EP2022/059010, filed Apr. 5, 2022, which claims priority to Netherlands patent application 2027928, filed Apr. 7, 2021, the entirety of which applications are incorporated by reference herein.

The invention relates to system for selectively supplying at least one and preferably two substances to a person, for example for regulating the concentration of glucose in the blood of a person. Such a system is known per se and may be used by diabetes patients for regulating the concentration of glucose in their blood. An example of such a system can be found in the international patent application WO2007/049961, but the system may be any other type of a system for selectively supplying at least one and preferably two substances to a person, for example for regulating the concentration of glucose in the blood of a person. For example, the system may be, but not limited thereto, an artificial pancreas, a bionic pancreas, a closed loop glucose control system, a low glucose suspend system, or a hybrid closed loop control system.

The system for selectively supplying at least one and preferably two substances to a person, for example for regulating the concentration of glucose in the blood of a person comprises:

- a device for selectively supplying said at least one and preferably two substances contained in respective at least one and preferably two reservoirs, said device comprising:
  - at least one and preferably two receiving spaces for accommodating a said reservoir,
  - at least one and preferably two ports for connecting to a transport element, and
  - a controller for controlling said device such that a certain amount of a said substance is supplied and thereby infused into the body of the person,
- at least one and preferably two infusion sets, a said infusion set comprising:
  - an infusion element comprising an infusion means for infusing a substance into a body of said person, said infusion means for example being a cannula, catheter, needle, or nozzle, said infusion means comprising an inlet end for receiving said substance and an outlet end for infusing said substance into said body, wherein said infusion element comprises a first connector for connecting to a second connector of a said transport element of the infusion set, and
  - a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means, and a third connector arranged at an inlet end of the transport means for connecting to a said port such that in a connected condition in which the third connector is connected to a said port a medium through flow connection is provided between a said reservoir accommodated in a said receiving space and the inlet end of the transport means for receiving a said substance from said reservoir.

Said system may alternatively be referred to as a set of components, i.e. said device and said at least one and preferably two infusion sets.

It is noted that said infusion set comprising said infusion element and infusion means may alternatively be referred to as an injection set comprising an injection element and injection means.

Said infusion means may either be partly inserted into the body of the person, for example in particular a said cannula, catheter or needle, or may be arranged close to the body and thereby able to infuse or inject the substance into the body, for example in particular a said nozzle.

Said substance may be infused or injected into the body over a longer period of time or instantaneously.

Each said receiving space may accommodate a respective reservoir.

The at least one infusion set of the system comprises disposable components and can be replaced for a new set by the user when needed, for example after a certain amount of time, for example a few days, or if any of the components of a said infusion set is obstructed or damaged.

It is known to perform a priming function when a new infusion set is used. Priming of the infusion set may mean that the transport element and in particular the transport means thereof and optionally also the infusion element and in particular the infusion means thereof is filled with a said substance prior to infusing substance into the body of the person, such that when a certain amount of substance is supplied by the device for infusion into the body of the person that amount of substance is actually infused into the person and will not, or at least for a limited amount, remain in the infusion set and/or such that no or a limited amount of air is infused into the body. Such a priming function or process may also be performed for flushing an infusion set, i.e. refilling the infusion set, for example in case air bubbles have been observed in the substance in the infusion set. The following text refers to the priming function only, but it will thus be clear that this same function can be used in a similar way for flushing the infusion set.

It is preferred that said priming function is performed when there is no medium through flow connection with the body of the person, such that it is impossible to infuse air or substance into the body during priming. This may improve the safety and/or convenience of use of the system.

It is an object of the invention to improve the system according to the invention such that the chance that the device is in a medium through flow connection with the body during priming is at least reduced.

This object may be achieved by a system as described above, any of the following parts of the system are defined to form at least one pair:

- the infusion elements and in particular the first connectors thereof, wherein at least two of said infusion sets are provided;
- the second connectors, wherein at least two of said infusion sets are provided;
- at least one second connector with said or a respective third connector, wherein at least one and preferably two of said infusion sets are provided;
- or any combination thereof, and in that said device is arranged to detect and/or be inputted with information indicating that said at least one pair is formed, and that the controller is arranged to control the device such that a priming function can only be performed if it is detected and/or inputted that said at least one pair is formed.

If said parts form said pair, it may be unlikely or even physically impossible that the infusion means are in a configuration that these can infuse substance or air into the body, i.e. the device is not in a medium through flow contact with the body. It can thus be prevented that the device is in a medium through flow connection with the body during priming, or the chance thereon is at least reduced.

In particular in case the infusion elements and in particular the first connectors thereof of the two infusion sets form a pair these may not or even cannot be attached to the body.

In particular if the second connectors of the two infusion sets form a pair these may not or even cannot be connected to the infusion elements.

In particular if at least one second connector and optionally or even preferably both of the second connectors form a pair with said or respective third connector, this or these second connector(s) may not or even cannot be connected to the infusion element(s), or if this or these second connector (s) are connected to the infusion element(s) the infusion element(s) may not or even cannot be attached to the body.

In this latter case at least the following three embodiments are within the scope of the claim. In a first embodiment said system comprises one infusion set and a priming function can only be performed if it is detected and/or inputted that the second connector thereof forms a pair with the third connector thereof. In a second embodiment said system comprises two infusion sets and a priming function can only be performed if it is detected and/or inputted that the second connector of one of the two infusion sets forms a pair with a third connector and preferably the third connector of the same infusion set. In a third embodiment said system comprises two infusion sets and a priming function can only be performed if it is detected and/or inputted that the second connectors of both infusion sets form a pair with a respective third connector.

If in the first two cases said one pair is formed and in the latter case said two pairs are formed the chance is reduced or it may be even be prevented that any of the in this example two infusion sets of the system is in a medium through flow connection with said body during priming, such that even in case only one of the in this example two infusion sets is to be primed, also the other infusion set is not in a medium through flow connection with the body. This further improves the safety and/or use of the device, because even in case the wrong infusion set out of the two infusion sets is primed there is no medium through flow with the body of that wrong infusion set. This is especially advantageous if it is inputted that said pair is formed, because the user may erroneously input that the pair is formed even when the wrong pair is formed. However, for a system for which a lower level of safety is acceptable or if a system is provided in which it is detected that said pair and preferably a correct pair is formed, there might be no need for the other infusion set that is not to be primed to also form said pair, although this would of course be possible. A correct pair may be understood here as a pair that is formed between the second and third connector of the same infusion set and in particular of the infusion set that is to be primed, It is noted that the second connector of a transport element preferably forms a pair with the third connector of that same transport element, i.e. a correct pair, but this is not required. The advantage is also obtained if the second connector forms a pair with the third connector of the other transport element, as long as it is the second connector of the infusion set to be primed that forms said pair. A respective third connector is thus not to be interpreted as the third connector of that same transport element, but only used to illustrate that in a case that both second connectors form a pair with a third connector these do not form a pair with the same third connector but each with a different third connector.

An advantage of the second connector(s) forming a pair together or with the third connector(s) is that the infusion element(s) may be or remain connected to the body during priming. This provides for example the advantage that only the transport element may be replaced and primed, while not replacing the infusion element(s). This is advantageous for the user because replacing the infusion element may be inconvenient because of the infusion means that, in most cases, needs to be inserted into the body.

An advantage of the first connectors forming a pair with each other is that also the infusion means thereof are primed.

It is noted that if a said pair is formed between two elements of the two different infusion sets, said pair is preferably formed in such a manner that the substances do not mix.

It is noted that the substance outlet end of the second connector or of the infusion element, dependent on which pair is formed, remains free during the priming function and when said pair is formed, such that the user is able to see that the substance arrives at or drips out of the substance outlet end or it may be detectable that the substance arrives at or drips out of the substance outlet end. The user may then end the priming function or the priming function may automatically end if the substance arrives at or drips out of the substance outlet end. Free outlet end may thus for example be understood here that the substance is able to drip out of the substance outlet end of the second connector or infusion element and is in particular not collected by any separate collecting or waste element. The substance outlet end of the second connector or infusion element is thus in particular not connected to a separate collecting or waste element for collecting waste substance during a priming function. It is further noted that optionally said second connector may have a waste collecting element that is an integral part of the second connector.

Said port may for example be defined by any suitable interface and/or connector for providing a connection between the device and third connector of the transport element. Said port is arranged in the vicinity of said or a respective receiving space, for example near a receiving end of said or a respective receiving space, such that when the or a respective third connector is connected to the or a respective port a medium through flow connection between the reservoir contained in the receiving space and the transport element is established.

Said controller may be any suitable type of controller, such as for example a (micro)processor.

Said (micro)processor may for example comprise a preprogrammed priming sequence.

Said device may alternatively be referred to as a pump.

Priming of the infusion set(s) may take place in any suitable manner. For example priming may take place manually, for example by the person inputting into the device to pump certain fixed amounts of substance until the substance appears at the outlet end of the transport means or infusion means, thereby indicating that the infusion set or part thereof is completely primed. Alternatively an automatic priming function may be performed wherein the priming process is automatically stopped once the infusion set is primed. Such an automatic priming function may for example be performed after the user inputting into the device to perform such automatic priming function. In such an automatic priming function said controller may be arranged to supply a known or calculated amount of substance or it may be detectable that said infusion set or part thereof is primed. Such manual or automatic priming functions are known to the skilled person.

It is noted that said device may further be arranged to detect and/or be inputted with information indicating that the third connector is and preferably both third connectors are connected to a said or a respective port, and wherein the controller is arranged to control the device such that a priming function can only be performed if it is detected and/or inputted that the third connector is and preferably both third connectors are connected to a said or a respective port. This makes sure that no priming function is performed when the transport element(s) is/are not even connected to the device.

In a simple embodiment of the system according to the invention a user may, optionally after being instructed to form said at least one pair or any other additional or alternative instruction directly or indirectly instructing the user to form said pair, input into the device that said at least one pair is formed or any other additional or alternative information indicating that at least one pair is formed, such as inputting into the device to proceed to a next step in and/or to start the priming process after forming said at least one pair, such that the device may then continue with the priming process by means of said controller controlling the device to supply said priming substance(s).

In such a simple embodiment the device may comprise an inputting means for inputting said information indicating that said at least one pair is formed. Such inputting means may for example comprise a touchscreen and/or at least one button and/or voice activation software. Such inputting means may optionally also be used for performing the manual priming process or for starting the automatic priming process.

This simple embodiment may improve the device as currently known, but it may be preferred if said device is arranged to detect whether said at least one pair is formed, because such an embodiment may eliminate human errors.

Detecting whether said at least one pair is formed may take place in any suitable way.

For example, in an embodiment of the system according to the invention said device is arranged to optically and/or electrically and/or electronically detect if said at least one pair is formed. In particular the controller of the device may be arranged to optically and/or electrically and/or electronically detect if said at least one pair is formed. In such an embodiment said device may comprise detection means for optically and/or electrically and/or electronically detecting if said at least one pair is formed and optionally said controller can be seen to form or be part of said detection means.

For example, in an embodiment of the system according to the invention at least one of the parts of said at least one pair comprises a detectable feature. Said feature may be an optically and/or electrically and/or electronically detectable feature. Optionally both parts of said at least one pair comprises such a detectable feature.

As a practical example, in an optical embodiment a light circuit may be closed when said at least one pair is formed, said closed light circuit being able to be detected by said device, in particular by the controller thereof. More in particular, light can be transmitted by the device, then transmitted through or via one of said transport elements and then returned to the device through or via the other transport element such that the device can detect the return light as a detection signal. The controller may be arranged to perform the priming function when and optionally as long as the return light is detected and until priming is completed. In this embodiment the light may be transferred from said one transport element to the other transport element via said infusion elements or the first connectors thereof and/or via the second connectors. In this embodiment the device and/or the infusion sets, in particular the transport elements thereof and optionally also the infusion elements, may comprise circuit parts that form said closed circuit in a state wherein said at least one pair is formed and when the third connectors are connected to the ports of the device. In such an embodiment the circuit part(s) of the device and/or the controller can be seen to form part of or define said detection means. In such an embodiment the circuit part(s) of the infusion sets can be seen as detectable features. In such an embodiment said parts of said pair are in contact with each other when these form said pair.

As an alternative or additional practical example, in an electronical and/or electrical embodiment an electricity circuit may be closed when said at least one pair is formed, said closed electricity circuit being able to be detected by said device, in particular by the controller thereof. More in particular, an electrical current can be transmitted by the device, then transmitted through or via one of said transport elements and then returned to the device through or via the other transport element such that the device can detect the return current as a detection signal. The controller may be arranged to perform the priming function when and optionally as long as the return current is detected and until priming is completed. In this embodiment the electrical current may be transferred from said one transport element to the other transport element via said infusion elements or the first connectors thereof and/or via the second connectors. In this embodiment the device and/or the infusion sets, in particular the transport elements thereof and optionally also the infusion elements, may comprise circuit parts that form said closed circuit in a state wherein said at least one pair is formed and when the third connectors are connected to the ports of the device. In such an embodiment the circuit part(s) of the device and/or the controller can be seen to form part of or define said detection means. In such an embodiment the circuit part(s) of the infusion sets can be seen as detectable features. In such an embodiment said parts of said pair are in contact with each other when these form said pair.

As an alternative or additional practical example, in an electronical embodiment said parts of said at least one pair may be arranged to provide and/or transmit an electronical signal or a specific electronical signal when these form said pair, which signal can be detected by said device and in particular the controller thereof as a detection signal. In such an embodiment at least one of the parts of said at least one pair may comprise at least one chip, for example an RFID chip, and the device, for example the controller thereof, may be arranged to read the chip(s). The electronical signal may be provided or transmitted wirelessly or non-wirelessly. For example, at least one of the parts of said at least one pair and/or the device may comprise a transmitter and/or an electromagnetic coil and/or other suitable communication means for transmitting and/or communicating and/or receiving said electronical signal. The controller may comprise receiving means for receiving said electronica signal. In such an embodiment the controller may define said detection means and/or said at least one chip may define the detectable feature. In such an embodiment the two parts may be arranged close to each other and/or be in contact with each other when these form said pair.

It is noted that said detection may take place purely electronically, electrically, or optically, or by any suitable combination thereof, and may optionally also be combined with other features, such as mechanical features.

For example, in a combined electronical, electrical or optical and mechanical embodiment a switch may be activated upon the parts being brought in contact with each other to form said pair, said switch for example closing an electronical, electrical or optical circuit, respectively.

Said controller may be arranged for detecting said detection signal, for example the return light, return current, or electronical signal.

Said controller may be arranged to perform said priming function upon said detection signal being detected and optionally as long as the detection signal is detected and/or detectable and until the priming function is completed.

In a specific embodiment of the system according to the invention in which the and preferably both second connector (s) is/are to form a pair with said and preferably a respective third connector, the electronical detection may provide a further advantage that it may be possible to determine whether the second and third connectors are the connectors of the same transport element. This may for example be achieved by said second and third connector each having a chip, for example a RFID chip, comprising for example same, similar or any other information suitable for this purpose, which information may be read by the controller as described above.

If said pair is formed said parts thereof may be arranged with respect to each other in any suitable way. For example, said parts may be arranged close and/or adjacent to each other. In such an embodiment it may not be required that said parts are in contact with each other, which may for example be suitable for an electronical embodiment as described above and/or if it is inputted into the device that said pair is formed.

In another embodiment of the system according to the invention the parts of said at least one pair are arranged to be brought in contact with and/or connected to each other.

Bringing the parts in contact with each other may be required for and/or enhance the communication between said parts, for example this may be required if said optical or electrical circuit is to be formed or in an electronical embodiment for enhancing the communication between said parts.

Connecting the parts to each other may aid bringing and/or keeping the parts in contact with each other, in particular in a correct manner and/or at a correct position and/or orientation.

In an embodiment of the system according to the invention said parts are arranged to be brought in contact with and/or connected to each other in such a manner that said infusion element or infusion elements cannot be in a condition being able to infuse substance into the body.

An advantage of such an embodiment is that it can be guaranteed that no air or substance can be supplied to the body during priming.

This can be achieved in different ways. For example, the second connectors of the transport elements may be brought in contact with each other and/or connected to each other in such a way, that these can physically not be connected to the first connector, thereby guaranteeing that there is no medium through flow connection between the transport element and the infusion element. For example, the second connectors may brought in contact with and/or connected to each other using their connecting means for connecting to the first connector.

As an alternative example, said and preferably both second connector(s) of the transport element(s) may be brought in contact with the or a respective third connector and/or connected thereto in such a way, that these cannot be connected to the first connector(s), thereby guaranteeing that there is no medium through flow connection between the transport element and the infusion element. For example, the second connector(s) may brought in contact with and/or connected to the third connector(s) using their connecting means for connecting to the first connector.

As a further alternative example, the infusion elements may be brought in contact with each other and/or connected to each other in such a way that that said infusion means cannot be in a position that it is possible to infuse said substance or air into the body, for example by connecting the sides from which the infusion means extend to each other or bringing these sides in contact with each other.

In an embodiment of the system according to the invention said system comprises connecting means for connecting the parts of said at least one pair to each other and/or the device.

Said connecting means may for example be part of at least one of said parts and/or of the device.

The connecting means may provide the advantage that said pairs are connected to each other and/or the device in such a manner that these form said pair and/or that it is detectable by the device that these form said pair.

Said connecting means may be chosen as desired. Said connecting means may for example comprise mutually cooperating connecting elements, such as a pin and hole, wherein at least one of said parts or the device has a pin and the other a hole. As an alternative example a snap fit connection may be used. Alternatively an adhesive or a loop and hook fastener can be used. Alternatively at least one of said parts or the device may be designed to be or comprise a female part being arranged to receive the other part or the device or a male part thereof.

In such an embodiment in which said parts may be connected to each other or the device using the connecting means the controller may be arranged to control the device such that a priming function can only be performed if it is detected or inputted that said parts are connected to each other or to the device.

The connecting means may be provided in such a manner that in a connected state of the parts the infusion elements cannot be in a configuration able to infuse substance into the body, for example as described above.

Said connecting means may in particular provide a releasable connection between the parts or the device.

In an embodiment of the system according to the invention said system comprises positioning and/or orientating means for positioning and/or orientating said parts in a certain position and/or orientation with respect to each other and/or the device.

Said positioning and/or orientating means may for example be part of the device and/or at least one of said parts.

The positioning and/or orientating means may provide the advantage that said pairs are positioned and/or oriented with respect to each other and/or the device in such a manner that these form said pair and/or that it is detectable by the device that these form said pair.

The positioning and/or orientating means may be chosen as provided. For example said positioning and/or orientating means may provide a ridge or the like against which said part(s) may abut such that it is in said desired position and/or orientation when abutting said ridge.

In an embodiment of the system according to the invention said device comprises an outputting means, such as a screen and/or a speaker, for outputting at least one instruction for the user, such as for example to form said at least one pair and/or to input said information indicating that said at least one pair is formed into the device and/or to not cancel the forming of said pair until a priming function is completely performed.

In an embodiment of the system according to the invention the device is arranged to:

- output a first instruction to the person to perform a priming process and/or be inputted by the person to start a priming process;
- output a second instruction, said second instruction instructing the person to form said at least one pair,
- detect and/or be inputted with information indicating that said at least one pair is formed;
- start the priming process after if it is detected or inputted that said at least one pair is formed It is noted that if no such first instruction is outputted but the person starts a priming process by himself without being instructed to do so, the second instruction can be seen as the first instruction.

First and second are thus not intended to be limiting in any way, but only used to be able to refer to these different instructions. In this respect it is further noted that any number of instructions may be outputted, also other, for example prior, intermediate, or later instructions.

It is noted that the first and second instructions can be a combined instruction instructing the person to perform a priming process and to form said at least one pair.

The priming process can be an automatic or manual priming process, as described above.

The invention also relates to the use of a system according to any of the preceding claims, comprising the steps of:

a) providing a system according to any of the preceding claims;
b) forming said at least one pair;
c) detecting and/or inputting information into the device indicating that said at least one pair is formed, and
d) performing a priming process.

It is noted that the steps can be performed in any suitable order and that additional steps may be performed before, in between, or after the steps.

Step b) may be performed in any suitable way, for example as described below. In step b) optionally two or more pairs may be formed.

Detecting that said at least one pair is formed may be performed by the device, as is described above with respect to the system according to the invention. Inputting the information into the device indicating that said at least one pair is formed may be performed by the person. Such information may for example be a confirmation inputted by the user that said at least one pair is formed and/or an input to start the priming process, wherein it is clearly outputted by the device to only start the priming process if said at least one pair is formed.

Step d) may be performed manually by the user inputting into the device to pump certain amounts of said substance(s) until the infusion set(s) is/are completely primed, or automatically by the device, for example after the user inputting the device to perform such automatic priming function.

In an embodiment of the use according to the invention a system according to claim 2 is provided in step a), wherein step c) comprises the step of inputting said information indicating that said at least one pair is formed by using the inputting means, for example by pressing a button and/or touching a touch screen and/or giving a voice instruction.

In an embodiment of the use according to the invention a system according to claim 3 is provided in step a), wherein step d) comprises the step of optically and/or electrically and/or electronically detecting that said at least one pair is formed.

Examples of these different and optionally to be combined ways of detecting that said at least one pair is formed are provided above with respect to the description of the embodiment of the system of claim 3. As described, such embodiments may be combined with any one or more other features, such as mechanical features, such as for example mechanical switch.

In such an embodiment step d) may optionally be performed continuously and/or regularly throughout the priming process, wherein the priming process is stopped as soon or when it is detected that said at least one pair is no longer formed.

In an embodiment of the use according to the invention a system according to at least claim 5 is provided, wherein step b) is executed by bringing the parts into contact with each other and/or connecting the parts to each other, optionally using the connecting means, optionally in such a manner that said infusion element or infusion elements cannot be in a condition being able to infuse substance into the body.

Advantages and examples of this embodiment are provided above with respect to the description of the embodiment of the system of claim 5, 6, or 7, where appropriate.

In an embodiment of the use according to the invention a system according to claim 8 is provided, wherein in step b) said parts are positioned an/or orientated in a certain position and/or orientation with respect to each other and/or the detection means using said positioning and/or orientating means.

Advantages and examples of this embodiment are provided above with respect to the description of the embodiment of the system of claim 8.

In an embodiment of the use according to the invention a system according to claim 10 is provided, comprising the steps of:

e1) outputting a first instruction, said first instruction instructing the person to perform a priming process, and/or e2) inputting to start a priming process;
f) outputting a second instruction, said second instruction instructing the person to form said at least one pair;
wherein steps c) and d) are performed after steps e1) and/or e2) and f).

Step e1) may be performed by the device, step e2) may be performed by the person. Step f) may be performed after step e1) and/or e). As described above with respect to the system of claim 10, if step e1) is not performed the second instruction can be the first instruction.

In accordance with a second invention of this application the second invention relates to a system for selectively supplying at least one and preferably two substances, for example for regulating the concentration of glucose in the blood of a person, comprising:

- a device for selectively supplying at least one and preferably two substances contained in respective at least one and preferably two reservoirs, said device comprising:
  - at least one and preferably two receiving spaces for accommodating a said reservoir,
  - at least one and preferably two ports for connecting to a transport element, and a controller for controlling said device such that a certain amount of a said substance is supplied and thereby infused into the body of the person, at least one and preferably two infusion sets, a said infusion set comprising:

an infusion element comprising an infusion means for infusing a substance into a body of said person, said infusion means for example being a cannula, catheter, needle, or nozzle, said infusion means comprising an inlet end for receiving said substance and an outlet end for infusing said substance into said body, wherein said infusion element comprises a first connector for connecting to a second connector of a said transport element of the infusion set, and a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means, and a third connector arranged at an inlet end of the transport means for connecting to a said port such that in a connected condition in which the third connector is connected to a said port a medium through flow connection is provided between a said reservoir accommodated in a said receiving space and the inlet end of the transport means for receiving a said substance from said reservoir, and comprising connecting means for connecting the at least one second connector to the third connector and/or the device.

The connecting means may be part of the second connector and/or third connector and/or the device.

Said connecting means may be chosen as desired. Said connecting means may for example comprise mutually cooperating connecting elements, such as a pin and hole, wherein one of said connectors or the device has a pin and the other a hole. As an alternative example a snap fit connection may be used. Alternatively an adhesive or a loop and hook fastener can be used. Alternatively one of said connectors or the device may be designed to be or comprise a female part that is arranged to receive the other connector or the device or a male part thereof.

Said connecting means may in particular provide a releasable connection between the second and third connector(s) and/or the device.

Said connecting means may in particular be provided such that in a connected condition of the second and third connector(s) and/or the device a substance outlet end of the second connector remains free, allowing substance to drip out of the substance outlet end of the second connector, for example during a priming process.

An advantage of this second invention is that the second connector(s) may temporarily be connected to the third connector(s) or the device, for example during priming as described with respect to certain embodiments of the first invention, but also at any other suitable moment. For example, when a user takes a shower the device and transport element(s) may be disconnected from the infusion element(s), such that the infusion element(s) may remain on the body but the device may be temporarily put away such that it does not get wet. In such a case it may be convenient to connect the second connector(s) to the third connector(s) or the device such that the transport element(s), which may have a relatively long length, does or do not dangle from the device but have a sort of stored position.

The second invention may also relate to an infusion set as described above with respect to the system according to the second invention.

In particular such an infusion set comprises:

an infusion element comprising an infusion means for infusing a substance into a body of said person, said infusion means for example being a cannula, catheter, needle, or nozzle, said infusion means comprising an inlet end for receiving a substance and an outlet end for infusing said substance into said body, wherein said infusion element comprises a first connector for connecting to a second connector of a said transport element of the infusion set, and a said transport element comprising a transport means, such as a conduit, tube, hose or the like, a second connector arranged at an outlet end of the transport means that is connectable to a said first connector of a said infusion element such that in a connected condition in which the second connector of the transport element is connected to the first connector of the infusion element a medium through flow connection is provided between the outlet end of the transport means and the inlet end of the infusion means for feeding the substance to the infusion means, and a third connector arranged at an inlet end of the transport means for connecting to a port of a device such that in a connected condition in which the third connector is connected to said port a medium through flow connection is provided between a reservoir accommodated in a receiving space of said device and the inlet end of the transport means for receiving a said substance from said reservoir, wherein the second connector and/or the third connector comprise connecting means for connecting the second connector to the third connector or a device.

The second invention also relates to such a package comprising at least one such an infusion set.

In an embodiment of the package the second connector is connected to the third connector by means of the connecting means.

The system and/or infusion set according to the second invention may comprise any one or more features as described above and below with respect to the system according to the (first) invention, in any suitable combination.

Figure 1B:
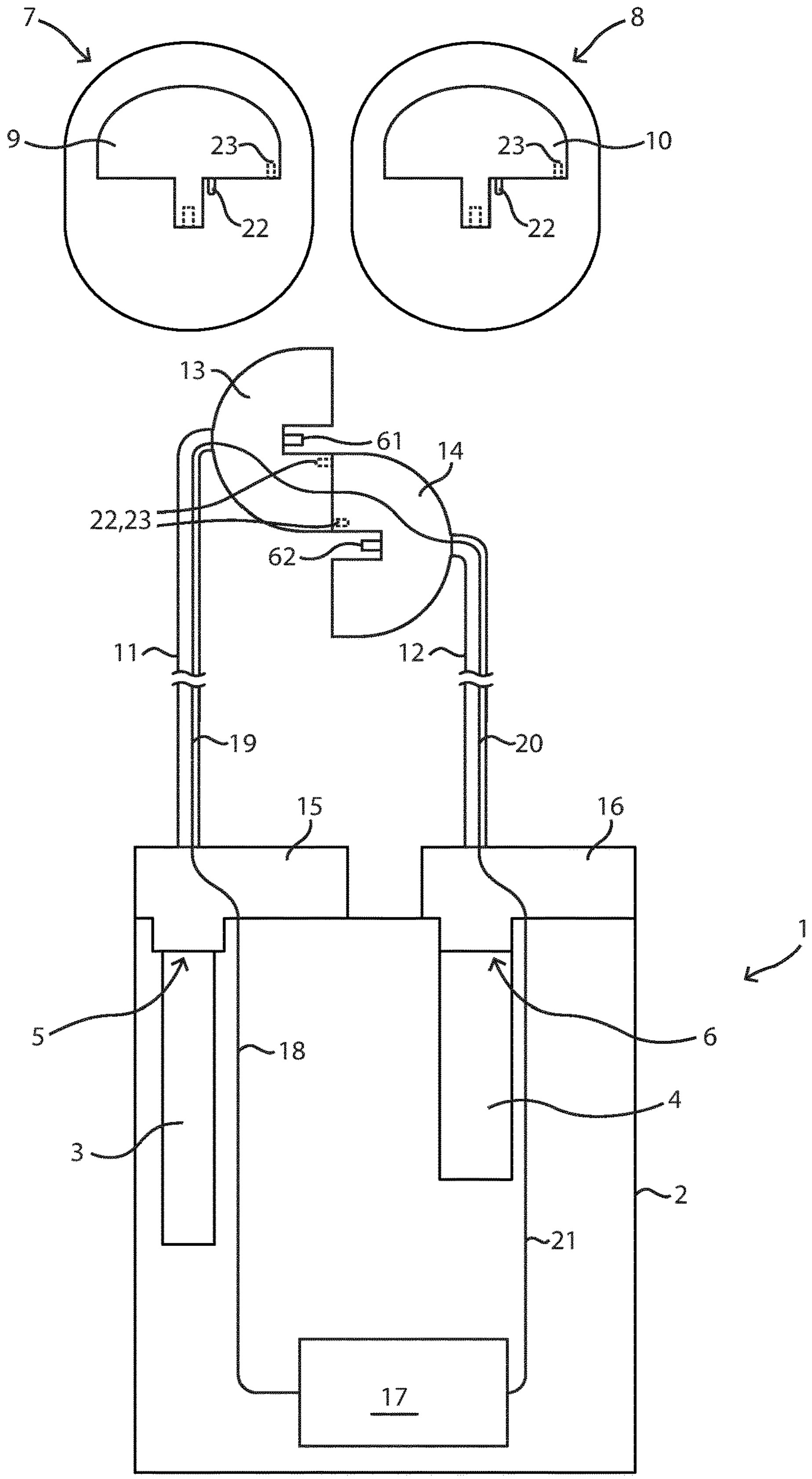
Figure 2A:
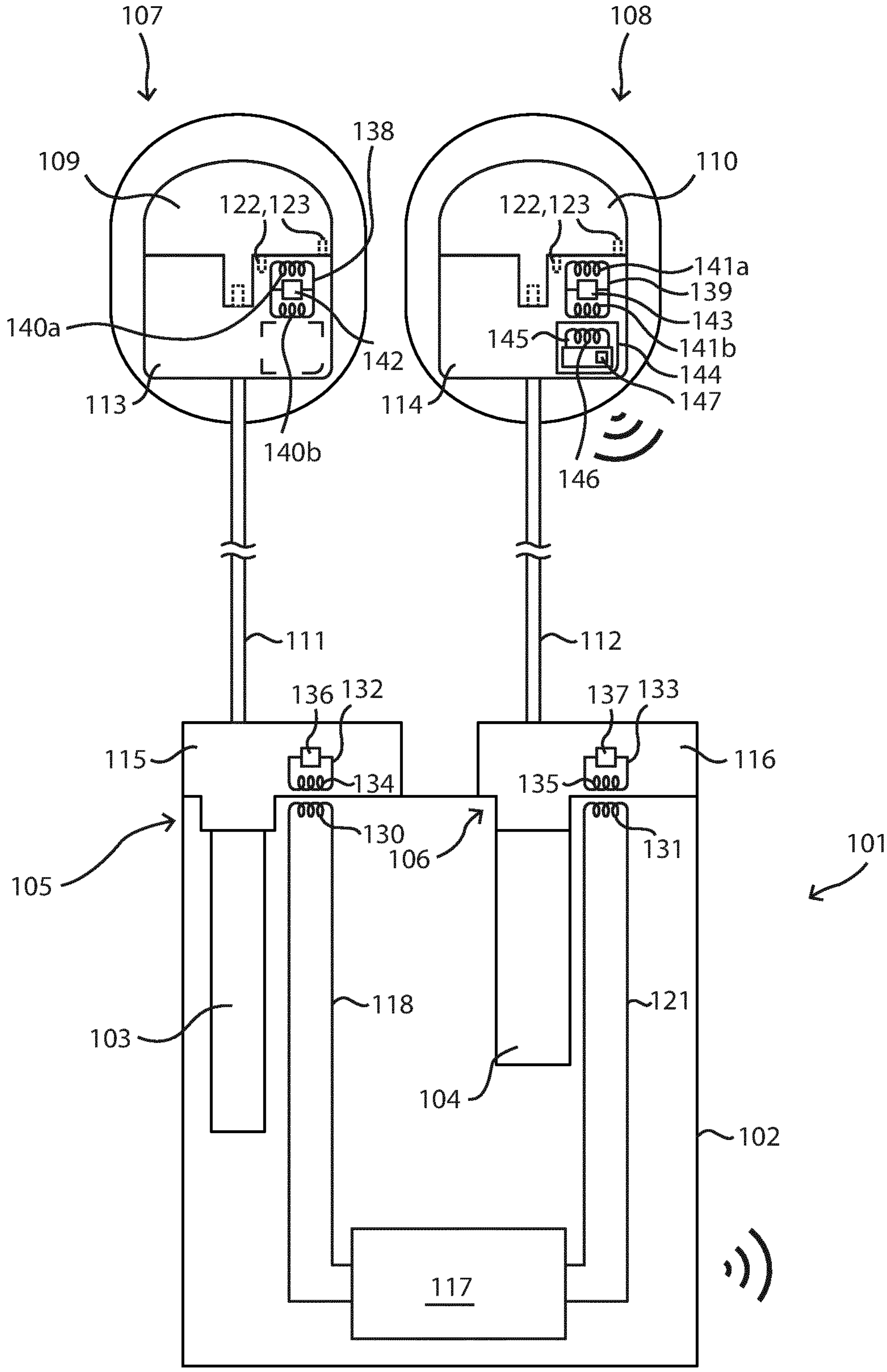
Figure 2B:
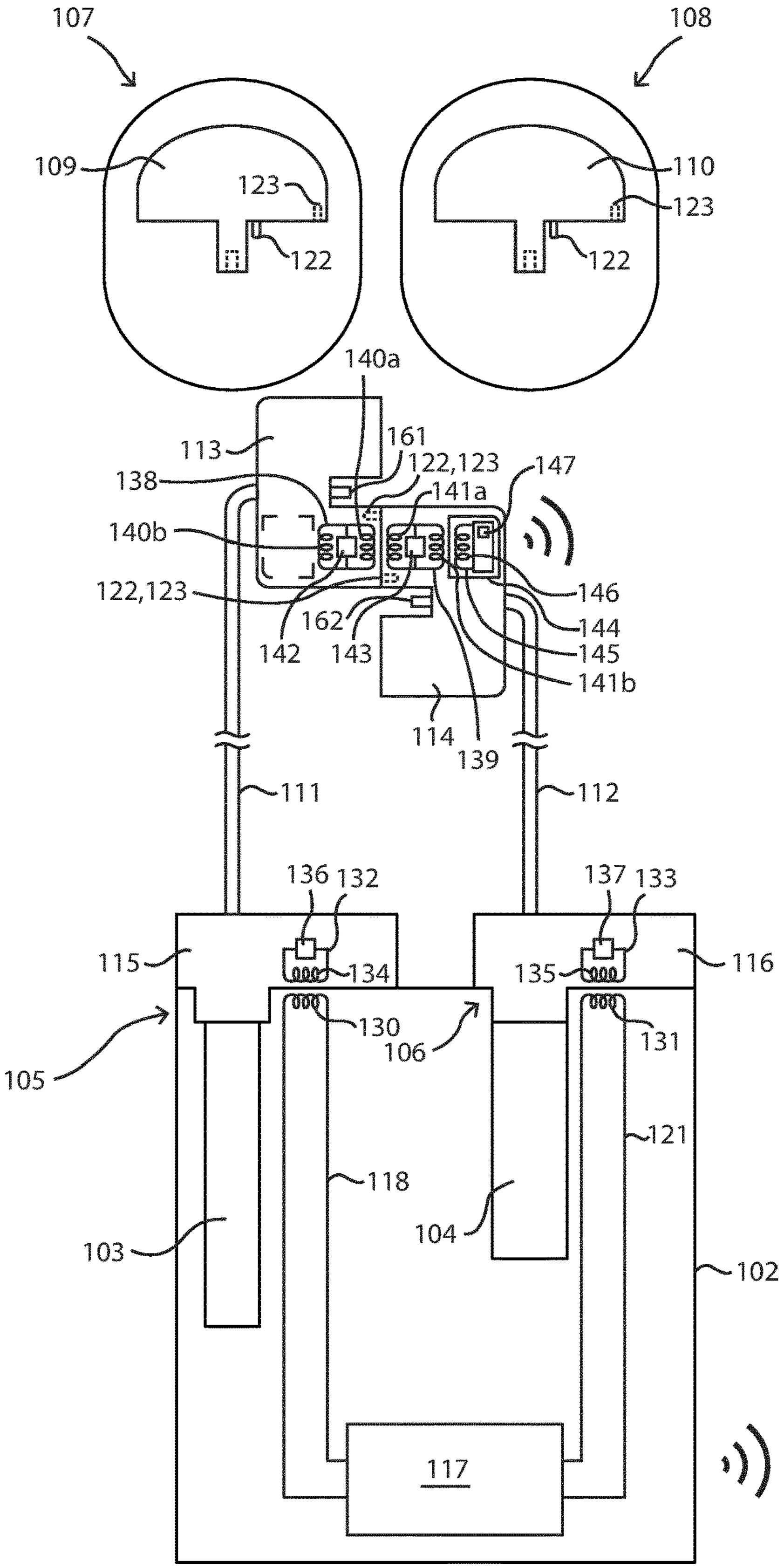
Figure 3B:
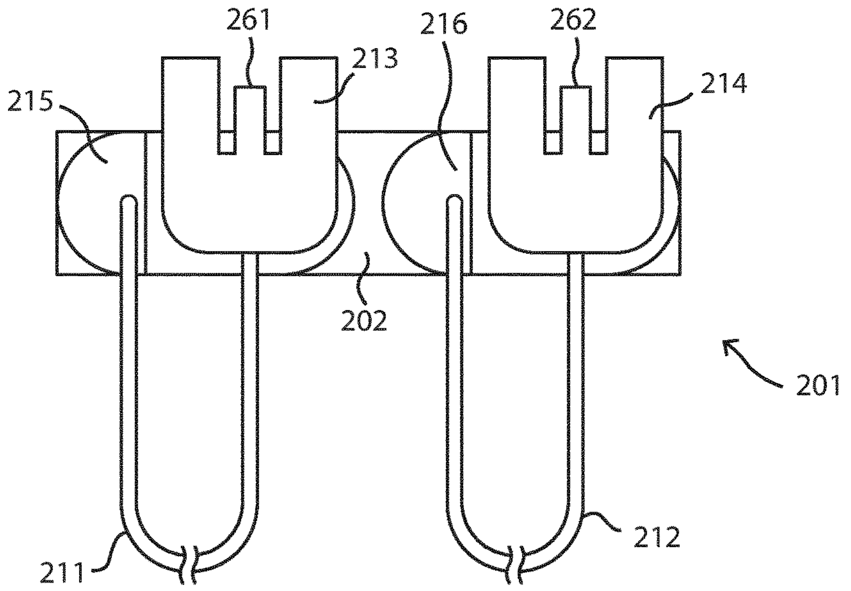
Figure 3A:
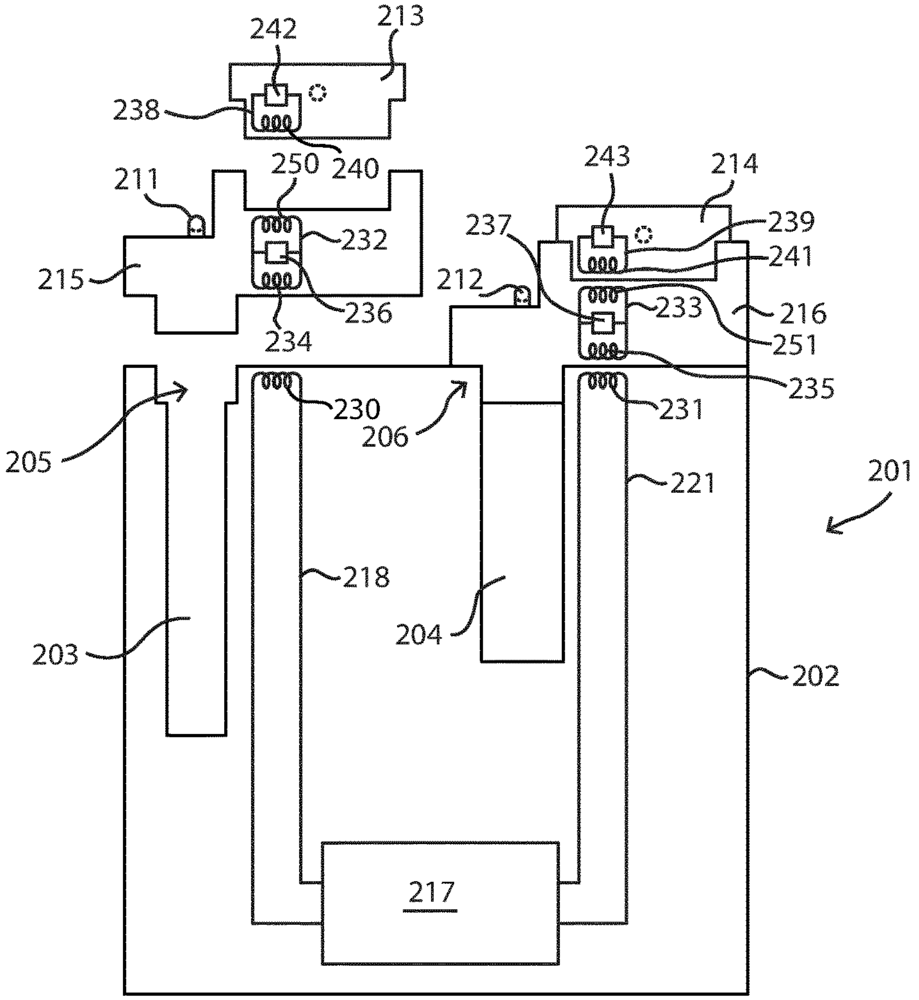
Figure 4:
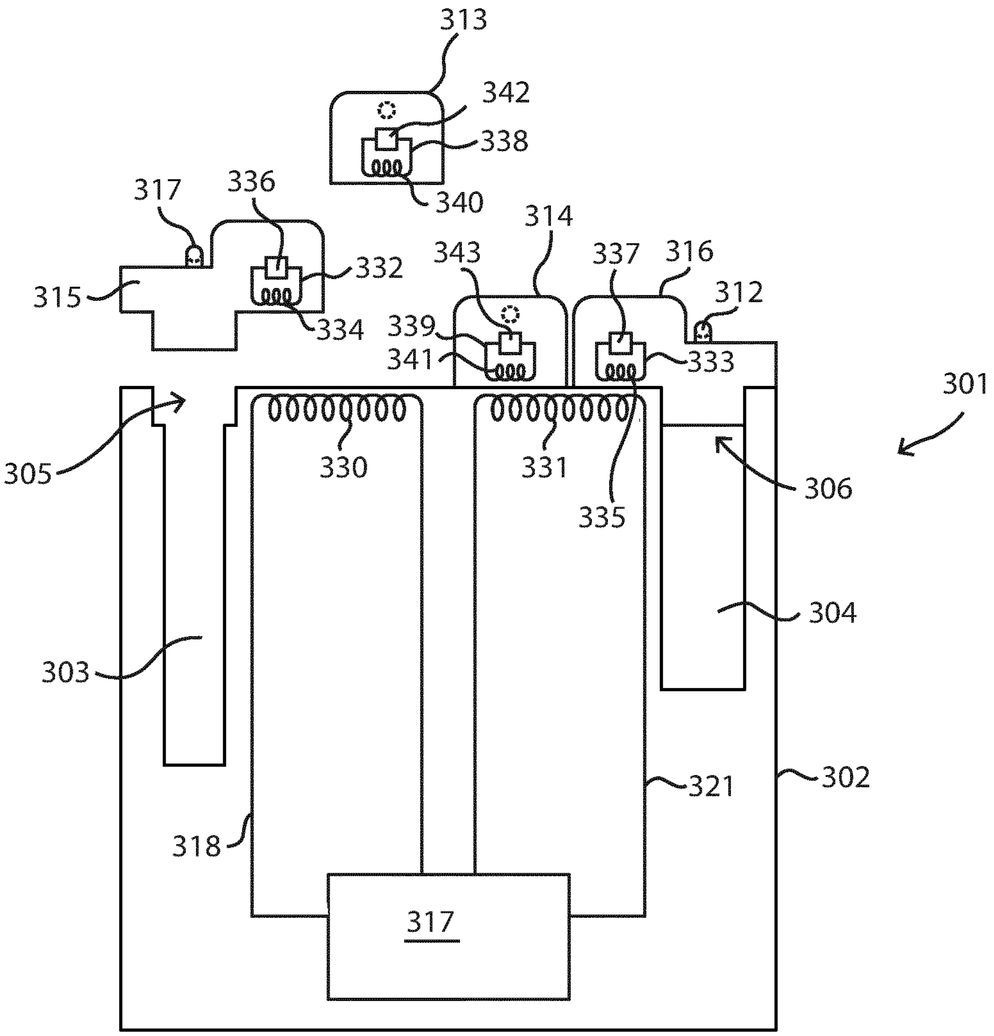

The invention(s) will be further explained with respect to figures, wherein:

FIGS. 1*a* and 1*b* schematically show a first embodiment of the system according to the invention, wherein FIG. 1*a* shows a state wherein no pair is formed and FIG. 1*b* shows a state wherein a said pair is formed;

FIGS. 2*a* and 2*b* schematically show a second embodiment of the system according to the invention, wherein FIG. 2*a* shows a state wherein no pair is formed and FIG. 2*b* shows a state wherein a said pair is formed;

FIGS. 3*a* and 3*b* schematically show a third embodiment of the system according to the invention, wherein FIG. 3*a* shows a front view and FIG. 3*b* a top view, and FIG. 4 schematically shows a fourth embodiment of the system according to the invention.

In the figures same or similar features are referred to by same reference numerals, increased by one hundred (100), two hundred (200) and three hundred (300) for the second, third and fourth embodiment, respectively.

For the sake of clarity and/or simplicity features that may be relevant for understanding the invention are shown in the figures, even though such features might not normally be visible in the views as shown. Further, some features of the system may not be shown for the sake of simplicity. The features that are shown may be shown in a simplified and/or enlarged way and/or in any other way different from reality but improving the readability of the figures.

FIGS. 1*a* and 1*b* show a schematic front view of a system 1 for in this example regulating the concentration of glucose in the blood of a person in two different conditions and/or states, as will be described below. Said system 1 comprises a device 2 for in this embodiment selectively supplying two substances, i.e. insulin and glucagon. Said device 2 comprises in this embodiment two receiving spaces 3, 4 for receiving and accommodating respective reservoirs containing said substances. As is shown in FIGS. 1*a* and 1*b*, in this embodiment the receiving spaces 3, 4 each have a different length and diameter, wherein the length and diameter are adapted to the type of reservoir to be received therein, such that each receiving space 3, 4 is able to receive only one type of reservoir. In particular, in this embodiment the receiving space 3 is able to receive an insulin reservoir and the receiving space 4 is able to receive a glucagon reservoir, which glucagon reservoir is shorter and thicker as compared to the insulin reservoir. The device 2 further comprises ports 5, 6, via which ports 5, 6 a respective reservoir may be inserted into the respective receiving space 3, 4 and to which an infusion set can be connected.

FIGS. 1*a*, 1*b* further show two infusion sets, wherein each infusion set comprises an infusion element 7, 8 comprising an infusion means for infusing a said substance into the body of said person, said infusion means for example being a cannula, catheter, needle, or nozzle, and said infusion means comprising an inlet end for receiving said substance and an outlet end for infusing said substance into said body. Such an infusion means is provided at the back of the infusion element 7, 8 as shown in FIGS. 1*a*, 1*b* and therefore not visible in FIGS. 1*a*, 1*b*. However, such an infusion element is well known to the skilled person and thus the skilled person would understand how to embody such an infusion means. The infusion elements 7, 8 further each comprise a respective first connector 9, 10.

In this embodiment each infusion set further comprises a respective tube 11, 12 as a transport means as part of a transport element. At an outlet end of the tubes 11, 12 each tube 11, 12 comprises a second connector 13, 14 that is connectable to a said first connector 9, 10 of a said infusion element 7, 8 such that in a connected condition as shown in FIG. 1*a* in which the second connectors 13, 14 are connected to the first connectors 9, 10 a medium through flow connection is provided between the outlet end of the tubes 11, 12 and the inlet end of the infusion means for feeding the substance to the infusion means. At an inlet end of the tubes 11, 12, which is located at the other end of the tubes 11, 12, said tubes comprise a respective third connector 15, 16 for connecting to a said port 5, 6 such that in a connected condition as shown in FIGS. 1*a*, 1*b* in which a said third connector 15, 16 is connected to a said port 5, 6 a medium through flow connection is provided between a said reservoir contained in a said receiving space 3, 4 and the inlet end of the tubes 11, 12 for receiving a said substance from a said reservoir. In the connected condition of FIG. 1*a* wherein the third connectors 15, 16 are connected to respective ports 5, 6 and the second connectors 13, 14 are connected to respective first connectors 9, 10 it is thus possible to feed a said substance to said person via a said tube 11, 12 and a said infusion element 7, 8.

Said device 2 comprises a controller 17 for controlling said device such that a certain amount of a said substance is supplied and thereby infused into the body of the person via a respective infusion set. For example said controller 17 may be used for performing a priming function, wherein at least the tubes 11, 12 are filled or flushed with substance. Said priming function may be a pre-programmed priming function or sequence stored in said controller.

In this exemplary embodiment the two second connectors 13, 14, i.e. one from each tube 11, 12, are defined to form a pair of parts, wherein in this embodiment the two second connectors 13, 14 can be brought into contact with each other and in this embodiment also connected to each other. FIG. 1*b* shows the state wherein said two second connectors 13, 14 form said pair. In this embodiment said device 2 is arranged to detect whether the second connectors 13, 14 form a pair by checking if these are in contact with and/or connected to each other as shown in FIG. 1*b*, and the controller 17 is arranged to control the device 2 such that a priming function can only be performed if it is detected that the two second connectors 13, 14 are in contact with each other. As is further shown in FIGS. 1*a*, 1*b* the two second connectors 13, 14 each comprise a fluid outlet 61, 62. Priming of any of the two transport means is completed if a said substance exits the respective outlet 61, 62 of that transport means. Said second connectors 13, 14 are preferably held by a user in such a manner that the substance does not drip on any component of the system 1.

In this embodiment it can be detected electrically or optically if the second connectors 13, 14 are in contact with each other. Electrical or optical circuit parts 18, 19, 20, 21 are provided, wherein circuit parts 18, 21 are provided within the device 2 and extend between the controller 17 and a respective port 5, 6, and wherein each transport element comprises a respective circuit part 19, 20 that extends along the respective tube 11, 12 from and including the respective third connector 15, 16 to and including the second connector 19, 20. If the respective tubes 11, 12 are connected to the respective ports 5, 6 using the respective third connectors 15, 16 and if the second connectors 13, 14 are connected to each other, the circuit parts 18-21 define a closed optical or electrical circuit. If said circuit is closed the controller 17 is able to transmit and receive an electrical or optical signal via said circuit, thereby being able to detect if the second connectors 13, 14 are in contact with and/or connected to each other and a priming function may be performed. If a signal is transmitted but not received, the controller 17 is able to detect that said second connectors 13, 14 are not connected to each other and no priming function is performed.

For connecting the second connectors 13, 14 to each other each second connector 13, 14 comprises mutual cooperating connecting means, in this embodiment defined by pin 22 and hole 23 connecting means. In this embodiment each second connector 13, 14 comprises both a said pin 22 and a said hole 23, wherein the pins 22 can be inserted into the holes 23 of the other second connector 13, 14. The first connectors 9, 10 also comprise similar pins 22 and holes 23, such that the second connectors 13, 14 can also be connected to the first connectors 9, 10 using the same connecting means.

As will be clear from FIG. 1*b*, the second connectors 13, 14 are connected to each other using the connecting means 22, 23 in such a manner, that these cannot be connected to the first connectors 9, 10 at the same time. This way it can be guaranteed that no substance and/or air can be infused into the body during priming.

It is noted that instead of the two second connectors 13, 14 being connected to each other, a similar solution can be foreseen in which the two first connectors 9, 10 are connected to each other. In such a case the first connectors 9, 10 may each comprise a circuit part, which circuit parts connect to the circuit parts 19, 20 at one end thereof and to each other at the other end thereof.

It is noted that instead of the two second connectors 13, 14 being connected to each other, a similar solution can be foreseen in which the second connectors 13, 14 connect to the third connectors 15, 16. In such cases the third connectors 15, 16 and the device 2 may comprise further circuit parts and in total two circuits will be closed when the second connectors 13, 14 are connected to the third connectors 15, 16. The controller 17 may check if the correct circuit or preferably both circuits are closed by transmitting and receiving (an) electrical or optical signal(s) and will be arranged to perform a priming process only if this is the case. Such an embodiment may also be suitably applied for a system in which only one infusion set is used, for example for a system supplying insulin only.

It is noted that a priming function may be stopped when the two second connectors 13, 14 are no longer in contact with and/or connected to each other, because in that case the electrical or optical circuit is broken which may be detected by the controller 17 and which may be arranged to stop the priming process in such a case.

FIGS. 2*a* and 2*b* show a second embodiment of the system 101. Only the differences with the first embodiment of FIGS. 1*a* and 1*b* will be described here. For a further description of the second embodiment of FIGS. 2*a* and 2*b* the reader is referred to the description of FIGS. 1*a* and 1*b*.

The second embodiment of the system 101 of FIGS. 2*a* and 2*b* differs in that it can be detected electronically if the two second connectors 113, 114 are in contact and in this case also connected to each other. The circuits 118, 121 of the device 2 are in this embodiment closed electrical or electronical circuits 118, 119 instead of circuit parts, wherein each circuit 118, 121 comprises a respective electromagnetic coil 130, 131. In this embodiment the third connectors 115, 116 of the transport element each comprise a closed electronical circuit 132, 133, each circuit 132, 132 comprising a respective coil 134, 135 and chip 136, 137, for example a memory chip. In this embodiment the second connectors 113, 114 of the transport element each comprise a closed electronical circuit 138, 139, each circuit 138, 139 comprising two coils 140*a*, 140*b*, 141*a*, 141*b*, and a respective chip 142, 143. A separately provided transmitter 144 may be releasably connected to in this example one of the two second connectors 113, 114, namely second connector 114. Said transmitter 144 comprises a closed electronical circuit 145 comprising a coil 146. Said transmitter further comprises a chip 147. Adjacent coil pairs, such as coils 130 and 134, coils 131, 135, coils 140*a*, 141*a*, and 141*b*, 146 allow for communication between the respective circuits. This way the controller is able to check if the third connectors 115, 116 are connected to the ports 105, 106 by reading the information stored in the respective chips 136, 137, and to check if the two second connectors 113, 114 form a pair by means of the transmitter 144 transmitting information stored in both chips 142, 143, which information can be wirelessly received by the controller 117. The controller 117 comprises receiving means for this purpose. Because the two chips 136, 137 are able to communicate with each other and the chip 137 is able to communicate with the transmitter 144, only one transmitter is required for the device to be able to detect if the two second connectors 113, 114 are in contact with and in this embodiment also connected to each other. Because said transmitter 144 is relatively costly it is advantageous that only one transmitter is required, even though it is of course possible that also second connector 113 is provided with such a releasable and therefor reusable transmitter.

An advantage of the third connectors 115, 116 and second connectors 113, 114 all having a chip is that said controller 117 may be arranged to check the information stored in said chips and thereby to determine if the second connectors 113, 114 are the second connectors of the transport element that is connected to the ports 105, 106 pump 102, and not second connectors of other transport element that are not connected to the ports 105, 106 of the pump 102. The chips 136, 142 of the one transport element on the one hand and the chips 137, 143 of the other transport element on the other hand may comprise same or similar information for this purpose.

Similar as for the first embodiment any suitable pair of parts can be formed in such an electronical embodiment, such as the first connectors 109, 110, or said second connectors 113, 114 with said third connectors 115, 116.

The transmitter 144 may further comprise a battery or any other suitable power source.

It is noted that even though some elements are disclosed to comprise a circuit comprising two coils, only one coil may be provided where applicable. This will be clear for the skilled person.

FIGS. 3*a* and 3*b* show a third embodiment of the system 201. Only the differences with the first and second embodiments of FIGS. 1*a*, 1*b*, 2*a*, 2*b* will be described here. For a further description of the third embodiment of FIGS. 3*a* and 3*b* the reader is referred to the description of FIGS. 1*a*, 1*b*, 2*a*, 2*b*.

The third embodiment of the system 201 of FIGS. 3*a* and 3*b* differs in that a pair is formed between the second connectors 213, 214 and a respective third connector 215, 216, which are in contact with and connected to each other. Said circuits 232, 233 of the third connectors 215, 216 each comprise a further coil 250, 251, that is able to provide communication with a respective circuit 238, 239 of a respective second connector 213, 214 via the respective coils 240, 241 thereof. Said controller 217 is able to detect if the second connectors 213, 214 form a pair with a respective third connector 215, 216 by checking the information as stored in the four chips 236, 237, 242, 243 if it receives all that information via the circuits 218, 221 and is further able to check if the second connectors 213, 214 are connected to a third connector 215, 216 of the same transport element by checking if the correct information pairs and thereby chip pairs are formed.

Because communication with the device 202 takes place via the coils, no transmitter is required in this third embodiment. All circuits may be powered via the device 202.

It is noted that if desired the chips 236, 237 of the third connectors 215, 216 may be omitted, because it may be detected that the second connectors 213, 214 are in contact with the third connectors 215, 216 if the controller 217 receives the information of only the chips 242, 243 of the second connectors 213, 214 as transmitted via the coils.

As is shown in FIG. 3*b* the second connectors 213, 214 are in this embodiment connected to the third connectors 215, 216 in such a manner that substance that may drip out of outlet ends 260, 261 of the transport element does not drop onto the device 202.

It is further noted that this third embodiment of the system 201 is described for an embodiment comprising two infusion sets, but this priming solution may also be used for an embodiment comprising only one infusion set, wherein the priming function may be performed when it is detected that the second connector and third connector of that infusion set form a pair.

It is further noted that if in the third embodiment of the system 201 as described above only one of the two infusion sets needs to be primed, it may be sufficient if only the second connector and third connector of the infusion set to be primed may form a pair. If it is detected that this pair is formed by checking the information stored in the chips of this pair, the priming function for priming this infusion set may be performed.

FIG. 4 shows a fourth embodiment of the system 301. Only the differences with the third embodiment of FIGS. 3*a* and 3*b* will be described here. For a further description of the fourth embodiment of FIG. 4 the reader is referred to the description of FIGS. 3*a* and 3*b*.

The fourth embodiment of the system 301 of FIG. 4 differs in that the second connectors 213, 214 that form a pair with a respective third connector 215, 216 are not in contact with, nor connected to each other, but are both in contact with and/or connected to the device 302 and are arranged adjacent to each other. The circuits 318, 321 of the device 302 are able to communicate with the circuits 332, 338, 339, 333 via the respective coils 334, 340, 341, 335 and by reading the information stored in the respective chips 336, 342, 343, 337 the controller 317 is able to detect if the two pairs are formed and if pairs are formed between the second and third connector of the same transport means or of different transport means.

It is noted that instead of providing two circuits 318, 321 the device 302 may alternatively comprise one circuit comprising at least one coil for communicating with the coils of the second and third connectors. Such an embodiment may be more simple by eliminating a circuit of the device 302, but in such a case the controller 317 if any of the two pairs is not formed the controller 317 is not able to check which pair is not formed, which is possible in the configuration shown in FIG. 4.

It is noted that optionally said device may comprise connecting means and/or positioning means and/or orientating means for connecting and/or positioning and/or orientating the second connectors with respect thereto, in particular in such a manner that the coils thereof are able to communicate with the at least one coil of the device.

It is noted that the invention is not limited to the shown embodiments but also extends to variants within the scope of the appended claims. For example, the system described in the shown embodiments is for regulating the concentration of glucose in the blood of a person, but for example by supplying different substance(s) the system may be used in a similar manner for a different purpose.

The invention claimed is:

1. A system for selectively supplying at least one substance to a person, comprising:

- a device for selectively supplying said at least one substance contained in respective at least one reservoir, said device comprising:
  - at least one receiving space for accommodating said reservoir,
  - at least one port for connecting to a transport element, and
  - a controller for controlling said device such that a certain amount of said substance is supplied and thereby infused into a body of the person,
- at least one infusion set, said at least one infusion set comprising:
  - an infusion element comprising an infusion means for infusing a substance into said body of said person, said infusion means comprising an inlet end for receiving said substance and an outlet end for infusing said substance into said body, wherein said infusion element comprises a first connector for connecting to a second connector of said transport element of the infusion set, and
  - said transport element comprising a transport means, said second connector arranged at an outlet end of the transport means that is connectable to said first connector of said infusion element such that in a connected condition in which the second connector of the transport element is connected to the first connector of the infusion element a medium through flow connection is provided between the outlet end of the transport means and the inlet end of the infusion means for feeding the substance to the infusion means, and a third connector arranged at an inlet end of the transport means for connecting to said at least one port such that in a second connected condition in which the third connector is connected to said at least one port a second medium through flow connection is provided between said reservoir accommodated in said receiving space and the inlet end of the transport means for receiving said substance from said reservoir,
- wherein at least one of the following parts of the system are defined to form at least one pair:
  - the infusion elements wherein at least two of said infusion sets are provided;
  - the second connectors, wherein at least two of said infusion sets are provided;
  - at least one second connector with said or a respective third connector, wherein at least one said infusion set is provided;
- or combinations thereof, and in that said device is arranged to detect and/or be inputted with information indicating that said at least one pair is formed, and that the controller is arranged to control the device such that a priming function can only be performed if it is detected and/or inputted that said at least one pair is formed;

- wherein a substance outlet end of the second connector or of the infusion element is free during the priming function and when said at least one pair is formed.

2. The system according to claim 1, wherein said device comprises an inputting means for inputting said information indicating that said at least one pair is formed.

3. The system according to claim 1, wherein said device is arranged to optically and/or electrically and/or electronically detect if said at least one pair is formed.

4. The system according to claim 3, wherein at least one of the parts of said at least one pair comprises a detectable feature.

5. The system according to claim 1, wherein the parts of said at least one pair are arranged to be brought in contact with and/or connected to each other.

6. The system according to claim 5, wherein said parts are arranged to be brought in contact with and/or connected to each other in such a manner that said infusion element or infusion elements cannot be in a condition being able to infuse substance into the body.

7. The system according to claim 1, further comprising connecting means for connecting the parts of said at least one pair to each other and/or the device.

8. The system according to claim 1, further comprising positioning and/or orientating means for positioning and/or orientating said parts in a certain position and/or orientation with respect to each other and/or the device.

9. The system according to claim 1, wherein said device comprises an outputting means for outputting at least one instruction for the person.

10. The system according to claim 1, wherein the device is arranged to:

output a first instruction to the person to perform a priming process and/or be inputted by the person to start said priming process;

output a second instruction, said second instruction instructing the person to form said at least one pair, detect and/or be inputted with information indicating that said at least one pair is formed; and start the priming process after if it is detected or inputted that said at least one pair is formed.

11. A use of the system according to claim 1, comprising the steps of:

a) providing the system;

b) forming said at least one pair;

c) detecting and/or inputting information into the device indicating that said at least one pair is formed, and d) performing a priming process.

12. The use according to claim 11, wherein in step a) the system further comprises an inputting means for inputting said information indicating that said at least one pair is formed, wherein step c) comprises the step of inputting said information indicating that said at least one pair is formed by using the inputting means.

13. The use according to claim 11, wherein in step a) system said device is arranged to optically and/or electrically and/or electronically detect if said at least one pair is formed, wherein step d) comprises the step of optically and/or electrically and/or electronically detecting that said at least one pair is formed.

14. The use according to claim 11, wherein in step a) the parts of said at least one pair are arranged to be brought in contact with and/or connected to each other, wherein step b) is executed by bringing the parts into contact with each other and/or connecting the parts to each other.

15. The use according to claim 11, wherein in step a) the system further comprises positioning and/or orientating means for positioning and/or orientating said parts in a certain position and/or orientation with respect to each other and/or the device, wherein in step b) said parts are positioned an/or orientated in a certain position and/or orientation with respect to each other and/or a detection means using said positioning and/or orientating means.

16. The use of a system according to claim 11, wherein in step a) the system is arranged to:

output a first instruction to the person to perform a priming process and/or be inputted by the person to start said priming process;

output a second instruction, said second instruction instructing the person to form said at least one pair, detect and/or be inputted with information indicating that said at least one pair is formed; and start the priming process after if it is detected or inputted that said at least one pair is formed;

further comprising the steps of:

e1) outputting a first instruction, said first instruction instructing the person to perform said priming process, and/or e2) inputting to start said priming process;

f) outputting said second instruction, said second instruction instructing the person to form said at least one pair;

wherein steps c) and d) are performed after steps e1) and/or e2) and f).

* * * * *